United States Patent [19]
Amplatz et al.

[11] Patent Number: 5,833,682
[45] Date of Patent: Nov. 10, 1998

[54] LIGHT DELIVERY SYSTEM WITH BLOOD FLUSHING CAPABILITY

[75] Inventors: Curtis A. Amplatz, St. Paul; Mark A. Rydell, Golden Valley; Robert J. Ziebol, Blaine, all of Minn.; Christopher H. Porter, Woodinville, Wash.; Michael Kasinkas, Plymouth, Minn.

[73] Assignee: Illumenex Corporation, Plymouth, Minn.

[21] Appl. No.: 697,530

[22] Filed: Aug. 26, 1996

[51] Int. Cl.⁶ ................................................ A61B 17/36
[52] U.S. Cl. ................................................ 606/15; 606/7
[58] Field of Search .................. 606/2, 7, 8, 10, 606/11, 12, 13, 14, 15, 16, 17

[56] References Cited

U.S. PATENT DOCUMENTS

| | | |
|---|---|---|
| Re. 34,544 | 2/1994 | Spears . |
| Re. 34,695 | 8/1994 | Mar et al. . |
| 4,266,548 | 5/1981 | Davi . |
| 4,336,809 | 6/1982 | Clark . |
| 4,469,098 | 9/1984 | Davi . |
| 4,470,407 | 9/1984 | Hussein . |
| 4,512,762 | 4/1985 | Spears . |
| 4,648,892 | 3/1987 | Kittrell et al. . |
| 4,660,925 | 4/1987 | McCaughan, Jr. . |
| 4,669,467 | 6/1987 | Willett et al. . |
| 4,791,926 | 12/1988 | Fry . |
| 4,799,479 | 1/1989 | Spears . |
| 4,862,886 | 9/1989 | Clarke et al. . |
| 4,878,492 | 11/1989 | Sinofsky et al. . |
| 4,961,738 | 10/1990 | Mackin . |
| 4,985,028 | 1/1991 | Isner et al. . |
| 5,053,033 | 10/1991 | Clarke . |
| 5,169,395 | 12/1992 | Narcisco, Jr. . |
| 5,196,005 | 3/1993 | Doiron et al. . |
| 5,207,669 | 5/1993 | Baker et al. . |
| 5,207,672 | 5/1993 | Roth et al. . |
| 5,242,438 | 9/1993 | Saadatmanesh et al. . |
| 5,342,298 | 8/1994 | Michaels et al. ........................ 604/65 |
| 5,370,608 | 12/1994 | Sahota et al. . |
| 5,411,466 | 5/1995 | Hess ........................................... 606/7 |
| 5,437,659 | 8/1995 | Leckrone .................................. 606/7 |
| 5,439,000 | 8/1995 | Gunderson et al. . |
| 5,441,497 | 8/1995 | Narcisco, Jr. . |
| 5,496,309 | 3/1996 | Saadat et al. . |
| 5,514,128 | 5/1996 | Hillsman et al. . |
| 5,620,438 | 4/1997 | Amplatz et al. ......................... 606/10 |
| 5,624,433 | 4/1997 | Radisch, Jr. .............................. 606/7 |

FOREIGN PATENT DOCUMENTS

688581A1 of 0000 European Pat. Off. .

*Primary Examiner*—Jennifer Bahr
*Assistant Examiner*—Sonya Harris-Ogugua
*Attorney, Agent, or Firm*—Haugen and Nikolai, P.A.

[57] ABSTRACT

A light delivery system for use in irradiating vascular tissue includes a balloon catheter with a working lumen for receiving an optical fiber therein and an inflation/flushing lumen adapted to receive a liquid at a proximal end and leading to a space defined within the balloon member attached to a distal end of the catheter. The balloon member has a pattern of holes or pores in the wall thereof through which the saline may flow when the balloon is inflated, causing any blood or other absorbing substances that may interfere with good radiant energy transmission to be flushed away from the treatment site.

65 Claims, 6 Drawing Sheets

LIGHT DELIVERY SYSTEM WITH BLOOD FLUSHING CAPABILITY

BACKGROUND OF THE INVENTION

I. Field of the Invention

This invention relates generally to surgical instruments for improving the outcome of percutaneous transluminal coronary angioplasty procedures, and more particularly to a light delivery system incorporating a means for irradiating a treatment site with radiant energy, e.g., U.V. or visible light, while simultaneously flushing the blood from the light path. It has been previously found that radiating the treatment site reduces the incidences of restenosis.

II. Discussion of the Prior Art

U.S. patent application Ser. No. 08/425,858, filed Apr. 20, 1995, and entitled "Method and Apparatus for Treating Vascular Tissue Following Angioplasty to Minimize Restenosis", which is assigned to applicant's assignee, provides a discussion of the prior art relating to known methods and apparatus for reducing the proliferation of smooth muscle cells at the site of a stenotic lesion that had earlier been subjected to balloon angioplasty by exposure of the treatment site to U.V. light. The system described and claimed in the above-referenced pending patent application constitutes an improvement over the prior art, especially in the manner in which the involved tissue is irradiated with U.V. light in a controlled fashion by a step-wise displacement of a radiant energy-emitting fiber. The disclosure contained in the aforereferenced application Ser. No. 08/425,858 is hereby incorporated by reference in the present application as if fully set forth herein.

In efforts to irradiate endothelial and intimal tissue with light following an angioplasty procedure, a difficulty has arisen in delivering light of low wavelength at an adequate intensity to the treatment site due to the presence of blood or other light absorbing substances between the light energy emitter and the tissue to be treated. While the apparatus disclosed in the aforereferenced pending patent application of applicant's assignee is effective in clearing the site of most blood due to the expansion of a balloon member against the wall of the vessel being treated, even the thin remaining layer of blood or blood contaminated saline trapped between the exterior of the balloon and the blood vessel drastically reduces the transmissivity of U.V. light at the desired wavelength. It has been found that even a lo concentration of blood in saline can reduce the transmissivity of U.V. light at a wavelength of 257 nm by 70% or more. Thus, a need exists for an improved system for irradiating the interior lining of a blood vessel to impart to the system the ability to expose the blood vessel tissue to radiant energy at a sufficiently high, efficacious intensity.

SUMMARY OF THE INVENTION

We have devised a light delivery system for irradiating an internal surface of a blood vessel or a light curable plastic stent material with light energy so as to inhibit restenosis. It comprises a balloon catheter having an expansible, elongated, balloon member coaxially disposed on and bonded to a distal end portion of an elongated, flexible, plastic tubular catheter body member. The catheter body member is designed to have a working lumen and an inflation lumen/flushing lumen that extend from a suitable hub assembly on the proximal end of the catheter body to the distal end portion of the catheter where the balloon is attached. The inflation/flushing lumen is in fluid communication with the interior of the balloon member. The balloon member includes a pattern of small pores or apertures that extend through the wall thereof. Thus, when a flushing liquid such as normal saline is injected into a port on the hub communicating with the inflation/flushing lumen, it will simultaneously expand the balloon to a predetermined O.D. dimension and perfuse through the pores of the balloon member to flush away any residual blood or other light absorbing substances that may be present between the surface of the balloon and the blood vessel at the treatment site. Inflation of the balloon to a high pressure provides the ability to force the stenotic lesion into the blood vessel wall.

In one embodiment, an optical wavelength in the form of an optical fiber or a bundle of such fibers having a light diffusing element at its distal end is inserted through the working lumen and advanced there along until the light diffusing member is aligned with the distal end portion of the catheter body member on which the porous balloon is bonded. By coupling the proximal end of the optical fiber to a suitable source of light energy, it is transmitted along the fiber or fibers and, upon reaching the diffusing member, the radiation is caused to exit through the wall of the balloon and irradiate the treatment site.

In accordance with a further feature of the invention, an additional pump may be used to perfuse normal saline solution through the working lumen and out the distal end of the catheter. By maintaining a very low positive flow of saline through the catheter, it effectively prevents blood or other body fluids from being drawn back into the catheter's working lumen as a guide wire or the optical fiber is advanced and/or retracted within the working lumen. Means are also provided for inhibiting entry of blood contaminated fluid from being drawn into the balloon upon its deflation.

To avoid the necessity of frequent inflation/deflation cycles to allow blood flow distal to the site being treated, in accordance with a still further embodiment, provision is made for perfusing blood through a lumen of the catheter and out its distal end. To preclude the blood-filled lumen or channel of the catheter body from creating a shadow on the wall of the blood vessel, plural optical fibers comprising a fiber-optic bundle are deployable about the outside diameter of the catheter body such that the blood-filled channel is surrounded by the light-emitting defusing elements.

DESCRIPTION OF THE DRAWINGS

These and other objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
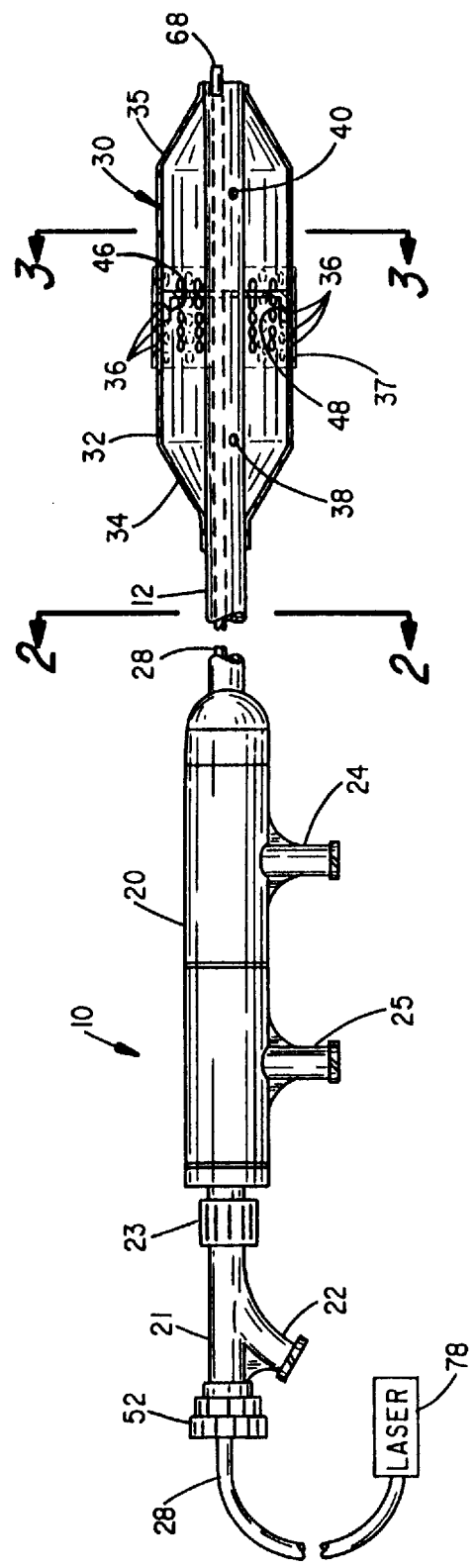
FIG. 1 is a side view, partially sectioned, of the light delivery system in accordance with one embodiment of the present invention.

With reference to FIG. 1, there is indicated generally by numeral 10 a light delivery system designed to apply radiant energy to the intimal and endothelial tissue of an artery or to a light curable plastic stent in the course of balloon angioplasty procedures on a patient. As in the device of the aforereferenced pending application Ser. No. 08/425,858, it comprises an elongated, flexible, tubular catheter body 12 which is preferably extruded from polyethylene plastic in that polyethylene plastic exhibits low loss properties as far as its ability to transmit light energy of a predetermined wavelength therethrough.

Figure 2:
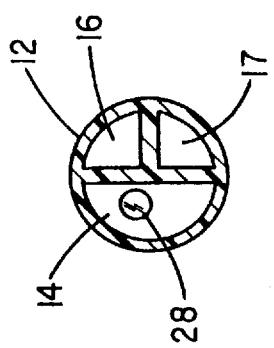
FIG. 2 is a cross-sectional view taken along the lines 2—2 in FIG. 1.

As can best be seen in the cross-sectional view of FIG. 2, the catheter body member 12 includes a plurality of lumens including a working lumen 14 and an inflation/ flushing lumen 16 and an optional perfusion lumen 17. Attached to the proximal end of the catheter body 12 is a molded plastic hub member 20 and a Y-adapter 21 defining a plurality of side entry ports 22 and 24. The side entry port 22 on Y-adapter 21 is in fluid communication with the working lumen 14 of the catheter body 12. Similarly, the side entry port 24 on hub member 20 is in fluid communication with the inflation/flushing lumen 16. If an optional perfusion lumen 17 is provided in the catheter 12, a further Luer fitting 25 is provided as a way of introducing a perfusate, e.g. blood, into the perfusion lumen. Each of the side entry ports includes a Luer fitting, allowing attachment of separate fluid sources thereto in a manner that will be further explained hereinbelow.

The Y-adapter 21 includes a rotatable fitting 23 cooperating with the hub 20 and a Touhy-Borst type clamp or seal 52 that cooperates with an optical fiber 28 to preclude fluid leakage. The optical fiber 28 extends through the Y-adapter 21 and the hub 20 and through the working lumen 14 of the catheter body 12.

Appropriately bonded to the exterior surface of the tubular catheter body 12 and spanning a distal end portion thereof is an inflatable expander member indicated generally by numeral 30 and comprised of an expansible balloon member 32. As is somewhat conventional with angioplasty balloons, the balloon 32 is generally cylindrical when inflated, such as is shown in FIG. 1, and it tapers at opposed ends 34, 35 to a lesser diameter, approximately that of the outside diameter of the catheter body member 12 where the balloon becomes bonded to the catheter body.

The balloon 32 is preferably made from a biaxially oriented polyethylene plastic material and would typically be about 1.5 mils thick. Balloons fabricated from fluorinated ethylene propylene (FEP), perfluoroalkoxy resin (PFA), polytetrafluoroethylene (PTFE), and ethylene-tetrafluoroethylene (ETFE) also exhibit desirable light transmissive properties in both the U.V. and visible light range. Located somewhat centrally in the cylindrical zone of the balloon 32 is a band containing a plurality of tiny apertures or pores 36, typically in a range of from 0.1 to 250 microns in diameter. Without limitation, for a balloon having a cylindrical zone approximately 20 millimeters in length, the band occupied by the plurality of pores may be centrally located and approximately 10 millimeters long.

Surrounding the expander member 30 and overlaying the porous band is a compliant elastomeric band 37 whose unstretched diameter is only slightly greater than the diameter of the tubular inner member 12. The elastic band 37 also includes a plurality of apertures that are laterally offset relative to the pores 36 formed through the wall 32 of the expander member 30. As will be explained in greater detail below, the perforated elastic band cooperates with the expander member during deflation thereof following initial inflation as a "check valve" to prevent infiltration of blood clouded saline into the interior of the expander member. While the apertures illustrated in the band 37 and in the underlying expander member 30 are illustrated as oval shaped or round, they may also comprise fine slits that will distend and open when pressurized to allow perfusion of saline therethrough, but which tend to reclose upon evacuation of the expander member.

Formed through the wall of the tubular catheter body 12 in the distal end portion thereof so as to be spanned by the expander member 30 are openings as at 38 and 40 which lead to the inflation/flushing lumen 16 in the catheter body.

Figure 3:
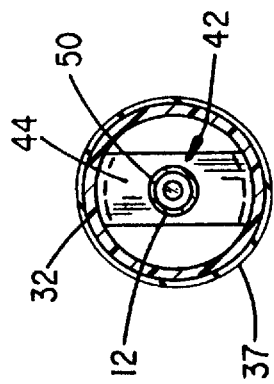
FIG. 3 is a cross-sectional view taken along the line 3—3 in FIG. 1.

As will be explained in greater detail below, to provide a more uniform exposure of a blood vessel wall to the U.V. light, it is deemed helpful to incorporate into the structure an anchoring arrangement for maintaining the distal end portion of the catheter body 12 centered midway within the confines of the expander member 30. If the distal end portion of the catheter is allowed to sag or droop, the optical path leading from the light fiber to the vessel wall becomes unsymmetrical. To avoid this condition, there is incorporated into the expander member 30 an anchoring structure 42 (FIG. 3). The anchoring structure may comprise a generally rectangular tab 44 of a thin flexible plastic sheet material having its opposed ends 46–48 (FIG. 1) bonded to the inside surface of the balloon member 32. Formed centrally in the tab 44 is a circular aperture 50 through which the distal end portion of the tubular catheter body 12 may pass. The tab 44 provides the requisite support for maintaining the catheter body 12 symmetrically suspended within the confines of the expansible balloon members when inflated.

Figure 4:
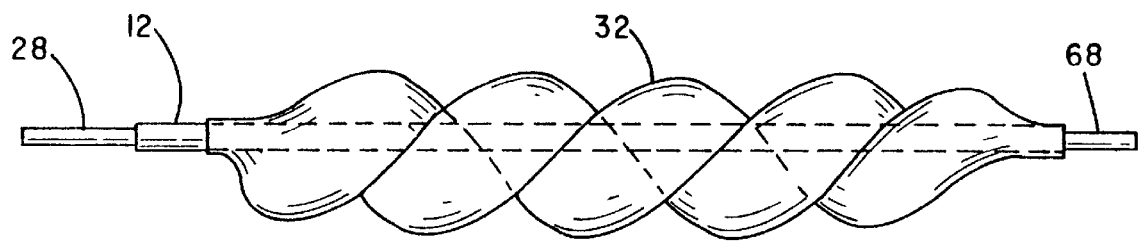
FIG. 4 is a view of a balloon incorporating a centering constriction.

An alternative centering approach is illustrated in FIG. 4. Here, as the balloon 32 is being formed from a parison, an insert in the mold employed imparts a constriction, preferably spiral in shape, to create a central spiraled neck or waist 51 in the balloon 32 for receiving the body member 12 therethrough and thereby centering same along the longitudinal axis of the body member 12 in a way somewhat similar to the technique disclosed in the Verin European Application 0,688,580 A1.

Figure 5:
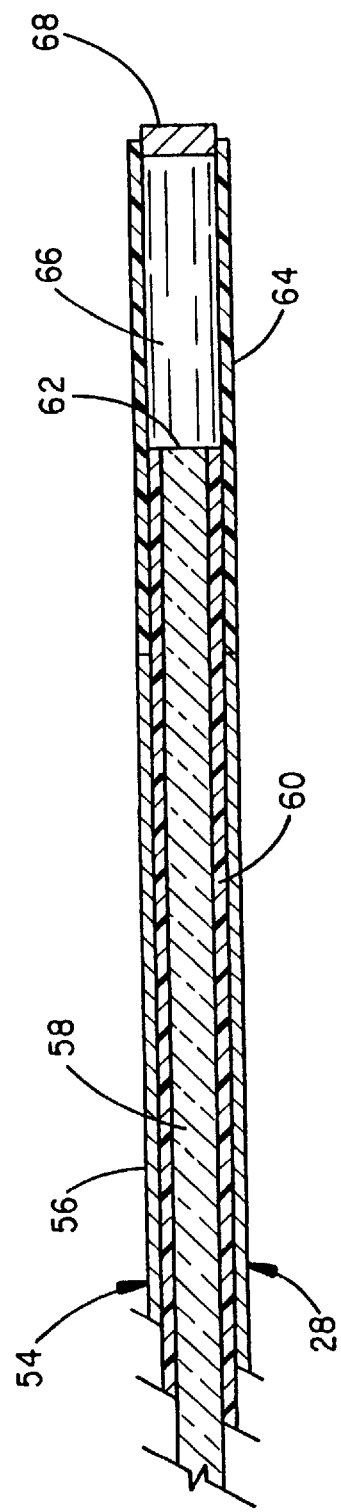
FIG. 5 is a longitudinal sectioned view of the optical fiber used in the system of FIG. 1.

Extending through the Touhy-Borst type compression fitting 52 and through the hub 20 and the working lumen 14 of the catheter body 12 is an elongated, flexible, radiant energy-transmissive fiber assembly 28. As is explained in the aforereferenced pending patent application Ser. No. 08/425,858, where the radiation source to be employed comprises a source of U.V. light, the radiant energy transmissive fiber may include a core member 54 (FIG. 5) comprising an outer stainless steel jacket 56 formed from a thin-wall hyperdermic needle stock and extending through the lumen thereof is a quartz fiber 58 which is surrounded by a polyimide jacket 60. The distal end of the quartz fiber 58, identified by numeral 62, is polished flat and held against its flat face, by means of shrink tubing 64, is a light diffuser 66 which, in the preferred embodiment, comprises a short length of Teflon® rod, which acts upon the light emanating from the distal end 62 of the light fiber to uniformly diffuse the light. In that considerable scattering of the light takes place without using the Teflon rod, it is not essential that the assembly 28 include such rod. A radiopaque marker comprising a tungsten plug 68 is also secured in place by the Teflon shrink tubing 64 so that the end of the light guide may be viewed fluoroscopically.

Having described the specifics of the construction of the light delivery catheter in accordance with a first preferred embodiment of the present invention, consideration will next be given to its mode of operation. In this regard, reference is made to the partially schematic drawing of FIG. 6.

In performing the angioplasty treatment, the light delivery catheter of FIG. 1, absent the light guide 28, is fed over a guide wire by inserting the proximal end of the guide wire into the distal end of the working lumen 14 of the light delivery catheter. The light delivery catheter is advanced over the guide wire until the distal end portion occupied by the expander member 30 is located adjacent the site of the stenotic lesion to be treated during the angioplasty procedure. Once the stenotic lesion has been compressed into the artery wall by inflation of the balloon 32 to a predetermined pressure, the pressure can be reduced somewhat and the guide wire can then be removed and replaced with the light fiber 28 which is fed through the Touhy-Borst clamp 52, the tubular hub 20 and the catheter body member 12 until the radiopaque distal end 68 is fluoroscopically determined to be located on the distal side of the treatment site.

As the light delivery catheter is being advanced over the guide wire, a roller pump 70 may be turned on to deliver a normal saline solution from a supply bag 72 to the inlet port 22 on the hub 20 leading to the working lumen 14 of the catheter body member. Saline is preferably delivered at a rate of about 2 milliters per minute which is an amount sufficient to insure that blood or other light absorbing substances will not flow back into the distal end of the working lumen of the catheter in a retrograde direction.

Now, by activating a positive displacement pump 74, normal saline from a supply bag 76 flows through the inlet port 24 and the inflation/flushing lumen 16 in the catheter body 12 to inflate the expander member 30 to a desired predetermined pressure which may be indicated by a suitable gauge, as at 77. When the pressure within the expander 30 exceeds the fluid pressure in the blood vessel, the normal saline can exude out through the tiny pores 36 formed in the wall of the balloon 32 and the band 37 to maintain a clear light transmission path essentially free of even trace amounts of blood in the zone between the exterior surface of balloon 32 and the surface of the blood vessel which it abuts.

With the roller pump 70 continuing to inject saline through the working lumen 14 of the light delivery catheter to prevent back flow of blood into the distal end of the catheter, the distal end portion of the optical fiber, including the diffuser 66, is moved reciprocally back and forth within the confines of the working lumen to provide a uniform exposure of the arterial tissue to the light transmitted from a laser source 78 through the quartz fiber 58 and the diffuser 66. In that the distal end portion of the catheter body 12 as well as the balloon are fabricated from a low-loss plastic material, e.g., polyethylene, FEP, PFA, PTFE or ETFE, and because the zone occupied by the expander member 30 has been flushed clear of all blood traces, efficient delivery of light energy to the tissue to be treated is achieved.

Figure 6:
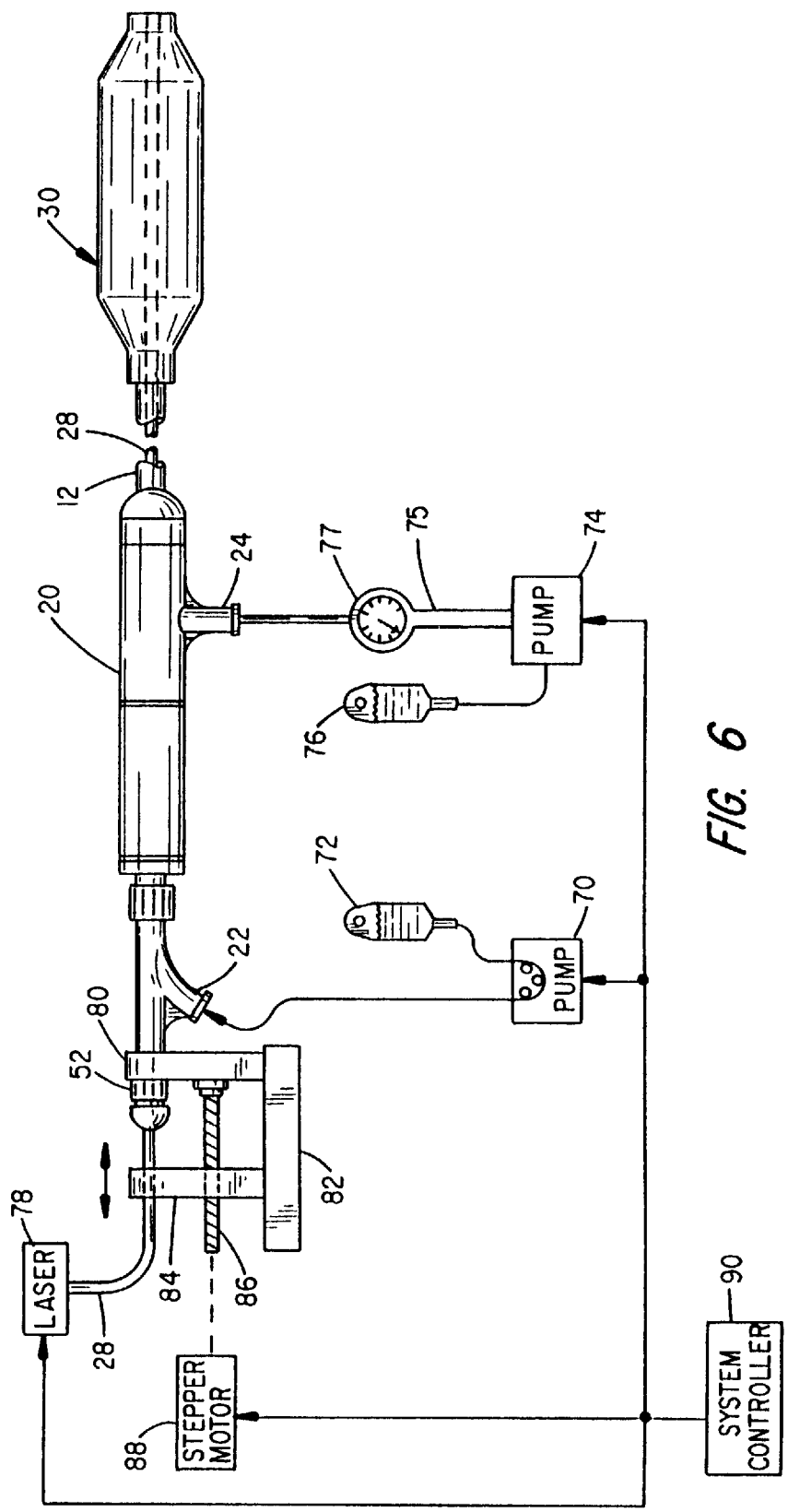
FIG. 6 illustrates schematically the manner in which the light delivery system illustrated in FIG. 1 is configured when in use.

With continued reference to FIG. 6, the reciprocal movement of the distal end of the optical fiber is achieved by clamping the hub 20 in a clamping fixture 80 affixed to a stationary base 82 and by clamping the optical fiber 28 in a slide member 84 which is movable along the stationary base 82 as indicated by the double-headed arrow. The slide member 84 comprises a traveling nut that is threaded onto a precision lead screw 86 which is adapted to be rotationally driven by a DC stepper motor 88. A system controller module 90 includes a microprocessor (not shown) that is programmed to precisely control the rotation of the lead screw and, therefore, the displacement of the diffuser member 66 along the distal end portion of the working lumen of the light delivery catheter body 12.

In addition to controlling the reciprocating movement of the optical fiber relative to the light delivery catheter, the system controller 90 may also be programmed to control the on/off state and the energy delivered by the laser 78 as well as the running of the roller pump 70 and positive displacement pump 74 for precisely controlling the amount of flushing liquid delivered through the working lumen 14 and the inflation/flushing lumen 16 of the catheter.

When it is necessary to reposition the light delivery catheter assembly within a blood vessel, the expander member must first be deflated. To prevent influx of blood-clouded saline into the interior of the expander member, the elastic band contracts with the deflation to effectively seal the pores 36 formed through the wall 32 of the expander member. In the event it becomes necessary to maintain the expander member 30 inflated for prolonged intervals in providing the desired tissue exposure, it may be necessary to permit blood to be perfused distal of the treatment site. In this event, the patient's own blood can be pumped via port 25 and the lumen 17 out the distal end of the catheter 12.

Figure 7:
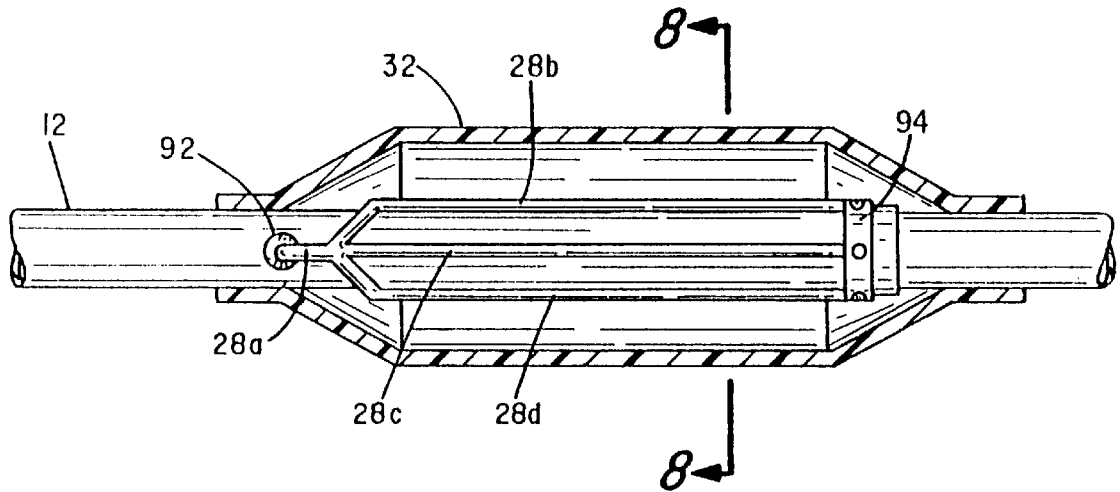
FIG. 7 depicts a view of an alternative embodiment allowing for blood perfusion during use of the light delivery system.
Figure 8:
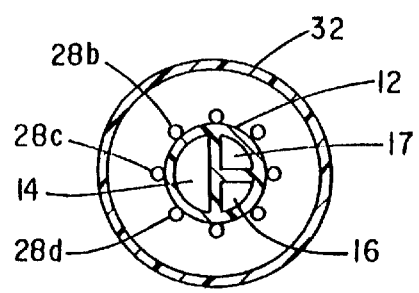
FIG. 8 is a cross-section of the view taken along the line 8—8 in FIG. 7.

The enlarged, partial side sectional view of FIG. 7 and the cross-sectional view of FIG. 8 illustrate an alternative embodiment of the invention where provision is made to avoid creating a shadow on the tissue wall to be treated when blood is being perfused through the perfusion lumen 17 of the catheter body member 12. Instead of employing a single optical fiber as at 28 in the embodiment of FIG. 1, a fiber-optic bundle 28*a* is made to traverse the working lumen 14 from its proximal end to an exit port 92 formed through the wall of the tubular member 12 at a location immediately distal of where the proximal end of the expander member 32 is bonded to the O.D. of the tubular member 12. The fiber-optic bundle 28*a* has its individual optical fibers 28*b*, 28*c* and 28*d* routed over the exterior surface of the tubular member 12 and the distal ends thereof are affixed to a slide ring 94 loosely surrounding the tubular member 12. In attaching the distal ends of the individual optical fibers 28*b*, 28*c* and 28*d* to the ring 94, the light-emitting surfaces thereof are appropriately directed to transmit light in the radial direction. During the course of the procedure, the stepper motor can be controlled so as to pull the proximal end of the fiber-optic cable in the proximal direction and thereby cause a corresponding translation of the ring 94 and the light-emitting distal ends of the individual fibers 28*a*–28*c* across the length dimension of the expander member and thereby illuminate the wall surfaces of the vessel being treated in accordance with a time/intensity profile programmed into the system controller 90.

While the foregoing procedure is taking place, the patient's blood, collected prior to the procedure, can be perfused through the perfusion lumen 17 of the tubular member 12 and out the distal end thereof to provide a blood supply to tissue located distally of the treatment site. Because the individual optical fibers 28*b*–28*d* effectively surround the perfusion lumen, no shadow thereof will be cast on the tissue to be treated.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A light delivery system for irradiating an internal surface of a blood vessel with light energy, comprising:
   (a) an elongated, flexible, tubular body member having a proximal end, a distal end portion and a plurality of lumens extending therebetween;
   (b) a hub member connected to the proximal end of the body member and having a plurality of ports connected individually to the plurality of lumens in the body member;
   (c) an inflatable member formed from a material generally transparent to light of a predetermined wavelength affixed to the distal end portion of the body member and in fluid communication with a first of the plurality of lumens for receiving an inflation fluid injected into one of the plurality of ports associated with the first of the plurality of lumens, the inflatable member including a plurality of pores for perfusing a portion of the inflation fluid therethrough at a rate sufficient to flush light absorbing substances from a zone in the blood vessel occupied by the inflatable member;
   (d) an elongated, flexible, light guide member having a proximal end adapted to be coupled to a source of light energy and a distal end portion having a light diffusing surface joined thereto, said light guide member being of a size to fit through a second of the plurality of lumens, allowing the light diffusing surface to be positionable within the inflatable member; and
   (e) means for controllably displacing the light diffusing surface longitudinally within the distal end portion of the tubular body member.

2. The light delivery system as in claim 1 wherein said inflatable member includes means for radially centering a distal end portion of the body member there within.

3. The light delivery system as in claim 2 wherein said means for radially centering the distal end portion of the body member comprises a flexible tab having opposed end portions bonded to an inner surface of the inflatable member at diametrically opposed locations and a centrally disposed aperture in the tab for receiving the distal end portion of the catheter body member therethrough.

4. The light delivery system as in claim 2 wherein said means for radially centering the distal end portion of the body member is comprised of an inflatable member that forms a spiral around the body member.

5. The light delivery system as in claim 1 and further including means for injecting a flushing liquid into one of said plurality of ports connected to a second of the plurality of lumens.

6. The light delivery system as in any one of claims 1–5 wherein the inflatable member is formed of a plastic selected from the class consisting of a polyethylene, FEP, PFA, PTFE, ETFE, PET, and nylon.

7. The light delivery system as in any one of claims 1–5 wherein the inflatable member is formed from an elastomer.

8. The light delivery system as in claim 7 wherein the elastomer material is selected from the group consisting of polyurethane, latex, and silicone.

9. The light delivery system as in any one of claims 1–5 wherein at least the distal end portion of the body member is of a material exhibiting a relatively low loss in transmission of light energy of the predetermined wavelength.

10. The light delivery system as in claim 9 wherein the material is PTFE.

11. The light delivery system as in any one of claims 1–5 wherein said plurality of pores are uniformly distributed in a circumferential band whose width is about one-half of a length dimension of the inflatable member.

12. The light delivery system as in any one of claims 1–5 wherein the size of the pores is between about 0.1 and 250 microns.

13. The light delivery system as in any one of claims 1–5 wherein the pores are slits.

14. The light delivery system as in any one of claims 1–5 and further including means cooperating with the inflatable member for inhibiting flow of blood into the inflatable member following inflation and during deflation thereof.

15. The light delivery system as in claim 14 wherein the inhibiting means comprises at least one elastic band overlying the inflatable member.

16. The light delivery system as in claim 15 wherein the at least one elastic band includes a plurality of pores laterally offset from the plurality of pores in the inflatable member.

17. The light delivery system as in any one of claims 1–5 wherein the plurality of pores are normally closed and open when pressure of the fluid injected into the one of the plurality of ports associated with the first lumen exceeds a predetermined value.

18. The light delivery system as in claim 17 wherein the pores are slits formed in the inflatable member.

19. The light delivery system as in any one of claims 1–5 and further including means for removing blood that may have entered the inflatable member.

20. The light delivery system as in claim 19 wherein the removing means includes means for increasing the flow of said fluid through said pores.

21. The light delivery system as in any one of claims 1–5 and further including a perfusion lumen in the tubular body member for permitting blood to flow past the inflatable member while it is inflated.

22. A light delivery system for irradiating an internal surface of a blood vessel with light energy, comprising:
   (a) an elongated, flexible, tubular body member having a proximal end, a distal end portion and a working lumen and an inflation lumen extending from a hub member on the proximal end to the distal end portion thereof;
   (b) an expansible, elongated, balloon member coaxially disposed on and bonded to the body member near the distal end portion, with the inflation lumen being in fluid communication with an interior of the balloon member, the balloon member adapted to be inflated by an inflation fluid injected into the inflation lumen, the balloon member including a plurality of pores of a predetermined size extending through a wall surface thereof for permitting a fraction of the inflation fluid to pass therethrough;
   (c) a waveguide having a proximal end connectable to a source of light energy and a distal end including a light diffusing member, the waveguide sized to fit through the working lumen of the body member such that the light diffusing member can be advanced into the distal end portion of the body member spanned by the balloon member; and
   (d) means coupled to the hub member and to the waveguide for controlled, step-wise displacement of the light diffusing member within the distal end portion of the body member spanned by the balloon member.

23. The light delivery system as in claim 22 and further including a first pump coupled to the hub for injecting a liquid into the inflation lumen.

24. The light delivery system as in claim 23 and further including a second pump coupled to the hub for injecting a liquid into the working lumen.

25. The light delivery system as in claim 22 wherein the distal end portion of the body member and the balloon member are light energy transmissive.

26. The light delivery system as in claim 25 wherein the distal end portion of the catheter body member and the balloon member are made of materials capable of transmitting light of a predetermined wavelength with less than about a 50 percent loss.

27. The light delivery system as in claim 26 wherein the materials are selected from a group consisting of polyethylene, FEP, PFA, PTFE, ETFE, PET, nylon, polyurethane, latex, or silicone.

28. The light delivery system as in claim 22 and further including balloon centering means for maintaining the balloon member concentrically centered on the distal end portion of the catheter body member.

29. The light delivery system as in claim 28 wherein the centering means comprises a flexible tab member disposed within the balloon member and having first and second opposed ends bonded to the balloon member at diametrically disposed locations and an aperture through the tab located midway between the first and second opposed ends, for receiving the catheter body member therethrough.

30. The light delivery system as in claim 29 wherein said means for radially centering the distal end portion of the body member is comprised of a balloon member that forms a spiral around the body member.

31. The light delivery system as in claim 22 and further including means cooperating with the balloon member for inhibiting flow of blood into the balloon member following inflation and during subsequent deflation thereof.

32. The light delivery system as in claim 31 wherein the inhibiting means comprises at least one elastic band overlying the wall surface of the balloon member.

33. The light delivery system as in claim 32 wherein the at least one elastic band includes a plurality of pores laterally offset from the plurality of pores in the inflatable member.

34. The light delivery system as in any one of claims 22–24 and 25–31 wherein the plurality of pores are normally closed and open when pressure of the fluid injected into the one of the plurality of ports associated with the first lumen exceeds a predetermined value.

35. The light delivery system as in any one of claims 22–24 and 25–31 wherein the pores are slits formed in the inflatable member.

36. The light delivery system as in any one of claims 22–24 and 25–31 wherein said plurality of pores are uniformly distributed in a circumferential band whose width is about one-half of a length dimension of the balloon member.

37. The light delivery system as in any one of claims 22–24 and 25–31 wherein the size of the pores is between about 0.1 and 250 microns.

38. The light delivery system as in any one of claims 22–24 and 25–31 wherein the pores are slits.

39. The light delivery system as in any one of claims 22–24 and 25–31 and further including means for removing blood that may enter the balloon member.

40. The light delivery system as in claim 39 wherein the removing means includes means for increasing the flow of said fluid through the pores.

41. The light delivery system as in claim 22 and further including a perfusion lumen in the tubular body member for permitting blood to flow past the balloon member while it is inflated.

42. A light delivery system for irradiating an internal surface of a blood vessel with light energy, comprising:
(a) an elongated, flexible, tubular body member having a proximal end, a distal end portion and a plurality of lumens extending therebetween;
(b) a hub member connected to the proximal end of the body member and having a plurality of ports connected individually to the plurality of lumens in the body member;
(c) an inflatable member formed from a material generally transparent to light of a predetermined wavelength affixed to the distal end portion of the body member and in fluid communication with a first of the plurality of lumens for receiving an inflation fluid injected into one of the plurality of ports associated with the first of the plurality of lumens, the inflatable member including a plurality of pores for perfusing a portion of the inflation fluid therethrough at a rate sufficient to flush light absorbing substances from a zone in the blood vessel occupied by the inflatable member, said plurality of pores being uniformly distributed in a circumferential band whose width is about one-half of the length dimension of the inflatable member; and
(d) an elongated, flexible, light guide member having a proximal end adapted to be coupled to a source of light energy and a distal end portion having a light diffusing surface joined thereto, said light guide member being of a size to fit through a second of the plurality of lumens, allowing the light diffusing surface to be positionable within the inflatable member.

43. A light delivery system for irradiating an internal surface of a blood vessel with light energy, comprising:
(a) an elongated, flexible, tubular body member having a proximal end, a distal end portion and a working lumen and an inflation lumen extending from a hub member on the proximal end to the distal end portion thereof;
(b) an expansible, elongated, balloon member coaxially disposed on and bonded to the body member near the distal end portion, with the inflation lumen being in fluid communication with an interior of the balloon member, the balloon member including a plurality of pores of a predetermined size extending through a wall surface thereof;
(c) a waveguide having a proximal end connectable to a source of light energy and a distal end including a light diffusing member, the waveguide sized to fit through the working lumen of the body member such that the light diffusing member can be advanced into the distal end portion of the body member spanned by the balloon member; and
(d) means coupled to the hub and to the waveguide for controlled, step-wise displacement of the light diffusing member within the distal end portion of the body member spanned by the balloon member.

44. The light delivery system as in claim 43 and further including a first pump coupled to the hub for injecting a liquid into the inflation lumen.

45. The light delivery system as in claim 44 and further including a second pump coupled to the hub for injecting a liquid into the working lumen.

46. The light delivery system as in claim 43 wherein the distal end portion of the body member and the balloon member are light energy transmissive.

47. The light delivery system as in claim 43 wherein the distal end portion of the catheter body member and the balloon member are made of materials capable of transmitting light of a predetermined wavelength with less than about a 50 percent loss.

48. The light delivery system as in claim 47 wherein the materials are selected from a group consisting of polyethylene, FEP, PFA, PTFE, ETFE, PET, nylon, polyurethane, latex, or silicone.

49. The light delivery system as in claim 43 and further including balloon centering means for maintaining the balloon member concentrically centered on the distal end portion of the catheter body member.

50. The light delivery system as in claim 49 wherein the centering means comprises a flexible tab member disposed within the balloon member and having first and second opposed ends bonded to the balloon member at diametrically disposed locations and an aperture through the tab located midway between the first and second opposed ends, for receiving the catheter body member therethrough.

51. The light delivery system as in claim 49 wherein said means for radially centering the distal end portion of the body member is comprised of a balloon member that forms a spiral around the body member.

52. The light delivery system as in claim 43 and further including means cooperating with the balloon member for inhibiting flow of blood into the balloon member following inflation and during subsequent deflation thereof.

53. The light delivery system as in claim 52 wherein the inhibiting means comprises at least one elastic band overlying the wall surface of the balloon member.

54. The light delivery system as in claim 53 wherein the at least one elastic band includes a plurality of pores laterally offset from the plurality of pores n the inflatable member.

55. The light delivery system as in claim 43 wherein the plurality of pores are normally closed and open when pressure of the fluid injected into the one of the plurality of ports associated with the first lumen exceeds a predetermined value.

56. The light delivery system as in claim 43 wherein the pores are slits formed in the inflatable member.

57. The light delivery system as in claim 43 wherein the size of the pores is between about 0.1 and 250 microns.

58. The light delivery system as in claim 43 wherein the pores are slits.

59. A light delivery system for irradiating an internal surface of a blood vessel with light energy, comprising:
  (a) an elongated, flexible, tubular body member having a proximal end, a distal end portion and a working lumen and an inflation lumen extending from a hub member on the proximal end to the distal end portion thereof;
  (b) an expansible, elongated, balloon member coaxially disposed on and bonded to the body member near the distal end portion, with the inflation lumen being in fluid communication with an interior of the balloon member, the balloon member adapted to be inflated by an inflation fluid injected into the inflation lumen, the balloon member including a plurality of pores of a predetermined size extending through a wall surface thereof, the plurality of pores being normally closed and open when pressure of the fluid injected into the one of the plurality of pores associated with the first lumen exceeds a predetermined value; and
  (c) a waveguide having a proximal end connectable to a source of light energy and a distal end including a light diffusing member, the waveguide sized to fit through the working lumen of the body member such that the light diffusing member can be advanced into the distal end portion of the body member spanned by the balloon member.

60. A light delivery system for irradiating an internal surface of a blood vessel with light energy, comprising:
  (a) an elongated, flexible, tubular body member having a proximal end, a distal end portion and a working lumen and an inflation lumen extending from a hub member on the proximal end to the distal end portion thereof;
  (b) an expansible, elongated, balloon member coaxially disposed on and bonded to the body member near the distal end portion, with the inflation lumen being in fluid communication with an interior of the balloon member, the balloon member adapted to be inflated by an inflation fluid injected into the inflation lumen, the balloon member including a plurality of pores of a predetermined size extending through a wall surface thereof, said plurality of pores being uniformly distributed in a circumferential band whose width is about one-half of a length dimension of the balloon member; and
  (c) a waveguide having a proximal end connectable to a source of light energy and a distal end including a light diffusing member, the waveguide sized to fit through the working lumen of the body member such that the light diffusing member can be advanced into the distal end portion of the body member spanned by the balloon member.

61. A light delivery system for exposing the interior wall of a blood vessel to light energy comprising:
  (a) an elongated, optical waveguide adapted to be connected at a proximal end to a source of light energy and having a light energy dispersing element at a distal end thereof;
  (b) a balloon catheter having an elongated flexible plastic catheter body having a proximal end, a distal end and a plurality of lumens extending therebetween and an inflatable expander member affixed to the catheter body at the distal end thereof, the expander member being in fluid communication with one of the plurality of lumens and the optical waveguide being insertable through another of the plurality of lumens, said means for flushing light absorbing substances comprising a plurality of fluid pervious pores formed in the expander member; and
  (c) means for flushing light absorbing substances from a zone between the energy dispersing element and the blood vessel wall at the treatment site.

62. The light delivery system as in claim 61 and further including means for inhibiting flow of blood clouded fluid through the pores formed in the expander member following inflation and subsequent deflation thereof.

63. The light delivery system as in claim 61 and further including means for removing blood that may have entered the expander member.

64. The light delivery system as in claim 61 wherein the elongated optical waveguide comprises a fiber-optic bundle including a plurality of optical fibers, said fiber optic bundle extending along said another of a plurality of lumens from the proximal end to an exit port formed through the catheter body at a location within the inflatable expander member, said plurality of optical fibers being routed over an outer surface of the catheter body at radially spaced locations.

65. The light delivery catheter as in claim 64 and further including slidable means surrounding the catheter body to which distal ends of the plurality of optical fibers are attached.

* * * * *